United States Patent
Heinrich et al.

(10) Patent No.: US 7,608,073 B2
(45) Date of Patent: Oct. 27, 2009

(54) ENERGY BASED PARTIAL CIRCUMFERENTIAL HEMORRHOID REPAIR DEVICE

(75) Inventors: Russell Heinrich, Madison, CT (US);
Scott Cunningham, Cheshire, CT (US);
Patrick Helfrich, Monroe, CT (US);
Tim Nolan, South Salem, NY (US)

(73) Assignee: Tyco Healthcare Group LP, North Haven, CT (US)

( * ) Notice: Subject to any disclaimer, the term of this patent is extended or adjusted under 35 U.S.C. 154(b) by 507 days.

(21) Appl. No.: 11/170,812

(22) Filed: Jun. 30, 2005

(65) Prior Publication Data

US 2006/0025766 A1    Feb. 2, 2006

Related U.S. Application Data

(60) Provisional application No. 60/586,778, filed on Jul. 9, 2004.

(51) Int. Cl.
*A61B 18/14* (2006.01)
(52) U.S. Cl. .......................... 606/50; 606/171
(58) Field of Classification Search ............ 606/48–52, 606/45–47, 205–209, 171; 227/179.1, 180.1
See application file for complete search history.

(56) References Cited

U.S. PATENT DOCUMENTS

| | | | |
|---|---|---|---|
| 1,586,645 A | 6/1926 | Bierman | |
| 4,304,236 A * | 12/1981 | Conta et al. ............... | 227/179.1 |
| 4,788,976 A * | 12/1988 | Dee ........................... | 606/167 |
| 4,985,030 A * | 1/1991 | Melzer et al. ............... | 606/51 |
| 5,057,107 A | 10/1991 | Parins et al. | |
| 5,104,025 A * | 4/1992 | Main et al. ............... | 227/175.1 |
| 5,201,900 A | 4/1993 | Nardella | |
| 5,207,691 A | 5/1993 | Nardella | |
| 5,360,154 A * | 11/1994 | Green ........................ | 227/179.1 |
| 5,360,428 A | 11/1994 | Hutchinson, Jr. | |
| 5,389,098 A * | 2/1995 | Tsuruta et al. ............... | 606/41 |
| 5,403,312 A * | 4/1995 | Yates et al. ................. | 606/50 |
| 5,445,638 A | 8/1995 | Rydell et al. | |
| 5,460,182 A | 10/1995 | Goodman et al. | |
| 5,467,911 A | 11/1995 | Tsuruta et al. | |
| 5,531,744 A | 7/1996 | Nardella et al. | |
| 5,582,611 A | 12/1996 | Tsuruta et al. | |
| 5,624,452 A | 4/1997 | Yates | |
| 5,655,698 A * | 8/1997 | Yoon ......................... | 227/176.1 |
| 5,665,085 A | 9/1997 | Nardella | |

(Continued)

FOREIGN PATENT DOCUMENTS

WO    WO 94/24951    11/1994

(Continued)

OTHER PUBLICATIONS

European Search Report for EP 05 01 4873, date of Completion of the search Aug. 26, 2005 (5 pgs).

*Primary Examiner*—Lee S Cohen

(57) ABSTRACT

An energy based partial circumferential hemorrhoid repair device including an actuator assembly, and an energy based partial circumferential hemorrhoid repair device head assembly operatively connected to the actuator assembly, wherein the head assembly includes a proximal electrode assembly and a distal electrode assembly, and further wherein at least one of the electrode assemblies includes an electrode mounted thereon to facilitate sealing of hemorrhoid tissue as the two electrode assemblies are approximated.

26 Claims, 8 Drawing Sheets

U.S. PATENT DOCUMENTS

| | | | |
|---|---|---|---|
| 5,688,270 | A | 11/1997 | Yates et al. |
| 5,693,051 | A | 12/1997 | Schulze et al. |
| 5,707,369 | A | 1/1998 | Vaitekunas et al. |
| 5,709,680 | A | 1/1998 | Yates et al. |
| 5,716,366 | A | 2/1998 | Yates |
| 5,735,848 | A * | 4/1998 | Yates et al. .................. 606/48 |
| 5,772,597 | A | 6/1998 | Goldberger et al. |
| 5,797,923 | A * | 8/1998 | Aiyar et al. .................. 606/129 |
| 5,810,811 | A | 9/1998 | Yates et al. |
| 5,833,690 | A | 11/1998 | Yates et al. |
| 5,846,241 | A * | 12/1998 | Kittur et al. .................. 606/48 |
| 5,876,401 | A | 3/1999 | Schulze et al. |
| 6,004,335 | A * | 12/1999 | Vaitekunas et al. .......... 606/169 |
| 6,024,741 | A * | 2/2000 | Williamson et al. ............ 606/40 |
| 6,027,514 | A * | 2/2000 | Stine et al. .................. 606/159 |
| 6,030,384 | A | 2/2000 | Nezhat |
| 6,119,913 | A * | 9/2000 | Adams et al. ............. 227/176.1 |
| 6,126,058 | A * | 10/2000 | Adams et al. ............. 227/180.1 |
| 6,142,933 | A * | 11/2000 | Longo et al. ................. 600/184 |
| 6,162,220 | A | 12/2000 | Nezhat |
| 6,193,716 | B1 | 2/2001 | Shannon, Jr. |
| 6,436,097 | B1 | 8/2002 | Nardella |
| 6,520,185 | B1 * | 2/2003 | Bommannan et al. ....... 128/898 |
| 6,527,771 | B1 * | 3/2003 | Weadock et al. .............. 606/50 |
| 6,629,630 | B2 * | 10/2003 | Adams .................... 227/180.1 |
| 6,638,233 | B2 * | 10/2003 | Corvi et al. ................. 600/564 |
| 6,805,273 | B2 * | 10/2004 | Bilotti et al. ............. 227/180.1 |
| 6,820,791 | B2 * | 11/2004 | Adams .................... 227/180.1 |
| 7,118,528 | B1 * | 10/2006 | Piskun ..................... 600/105 |
| 2003/0019905 | A1 * | 1/2003 | Adams et al. ............ 227/176.1 |
| 2007/0288043 | A1 * | 12/2007 | Rehnke ..................... 606/170 |

FOREIGN PATENT DOCUMENTS

| | | |
|---|---|---|
| WO | WO 99/25255 A | 5/1999 |
| WO | WO 99/62414 A | 12/1999 |

\* cited by examiner

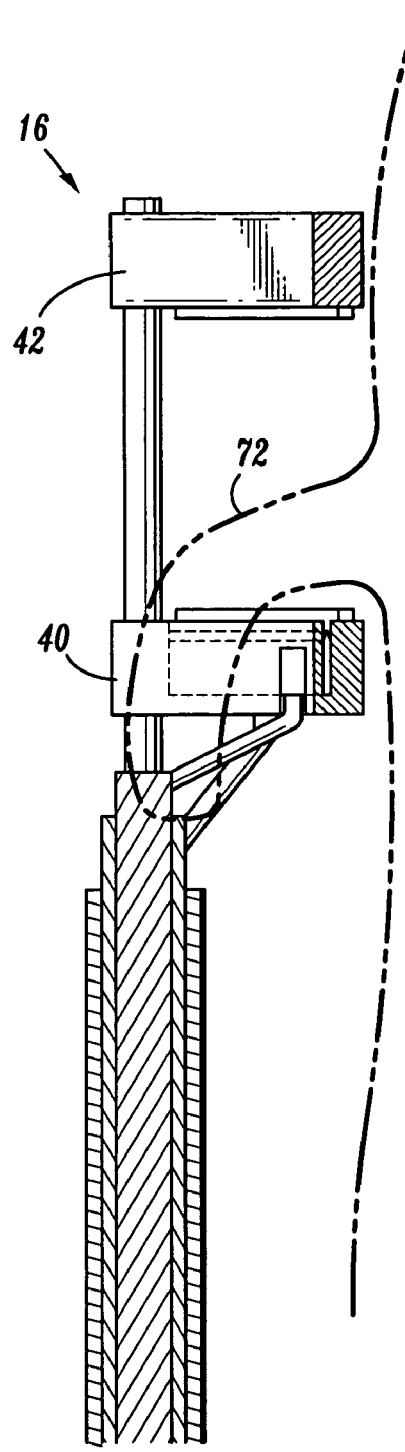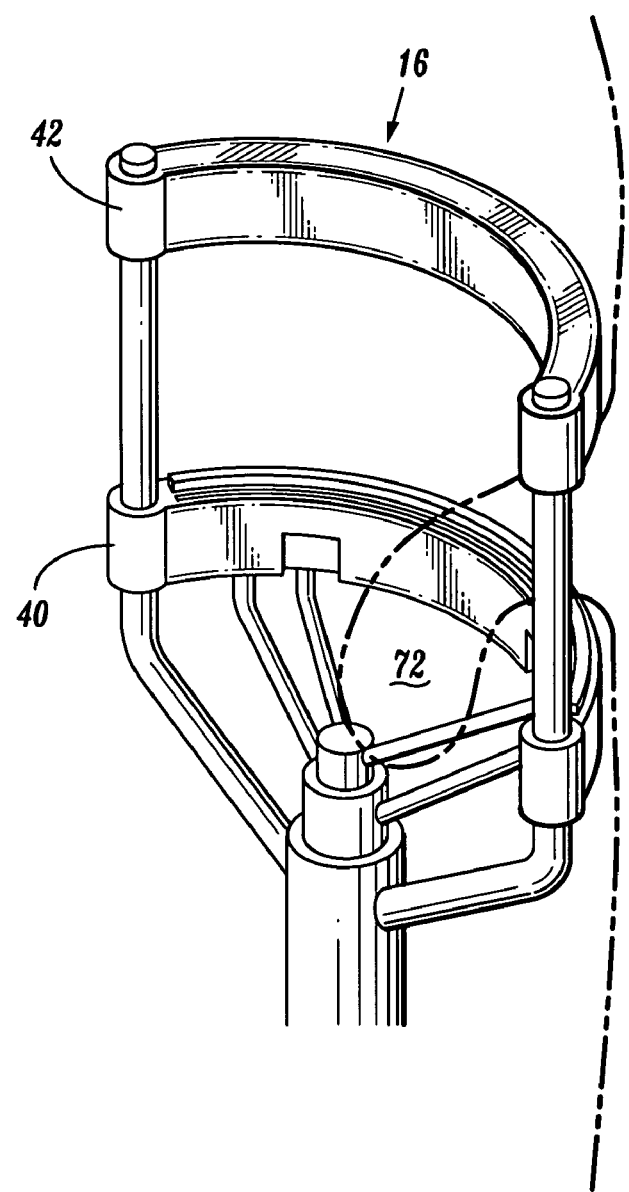
FIG. 6a
FIG. 6b

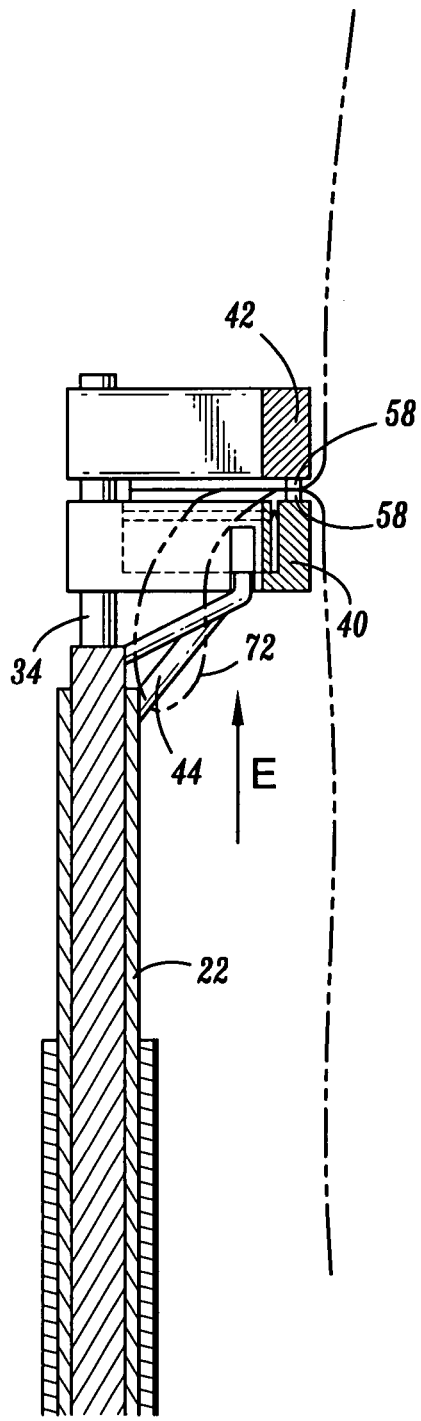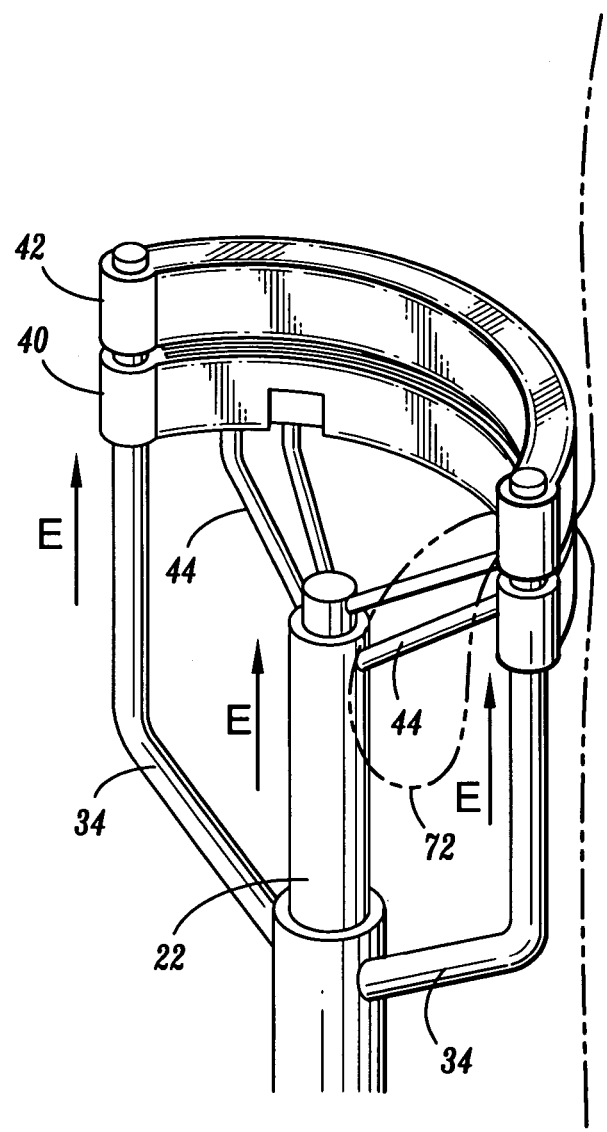
FIG. 7a
FIG. 7b

ENERGY BASED PARTIAL CIRCUMFERENTIAL HEMORRHOID REPAIR DEVICE

CROSS REFERENCE TO RELATED APPLICATIONS

This application claims the benefit of and priority to U.S. Provisional Application Serial No. 60/586,778 filed on Jul. 9, 2004 entitled "ENERGY BASED PARTIAL CIRCUMFERENTIAL HEMORRHOID REPAIR DEVICE", the entire contents of which are hereby incorporated herein by reference.

BACKGROUND

1. Field of the Disclosure

The present disclosure relates to an instrument for use in treating hemorrhoids, and more particularly to an energy based device for cutting and sealing hemorrhoid tissue.

2. Background of Related Art

Hemorrhoids are a swollen twisted mass of varicose veins that are located just inside the anus. Hemorrhoids are caused by chronic straining from, for example, constipation and childbirth. Chronic straining damages the valves located within the veins, and venous blood collects and distends the veins to many times the normal size. The slow flow of blood within the vein can cause additional injury to the vein, as well as thrombosis. As the patient ages, the elasticity of the tissue of the anus changes and the hemorrhoidal condition can worsen causing prolapse and anal bleeding. While rarely fatal, hemorrhoids are often painful. Treatments can range from heat packs and bed rest (in mild cases), to surgery (in extreme cases).

Hemorrhoids can be of two types, external and internal. A ribbed line is located 2.5-3 cm in from the exterior of the anus and marks the change from the anus to the rectum. External hemorrhoids are found in the anal area below this line and internal hemorrhoids are found in the rectal area above this line. Internal hemorrhoids are generally formed from an internal rectal venous plexus that resides in a submucosal space within the wall of the rectum, approximately 2.5 to 5 cm in from the exterior of the anus. It is a feature of the human anatomy that the venous plexus has three main venous branches or groups located circumferentially around the anus and rectum, and that hemorrhoids usually occur at one or more of these branches. Thus, internal hemorrhoids can protrude from the wall of the rectum in one localized area, more than one localized area, or circumferentially. In severe cases, the internal hemorrhoids can protrude out of the anus.

Internal hemorrhoids are rated by severity from a mild case (first degree) to a much more severe case (fourth degree). First and some second degree cases can be treated by injection or ligation (elastic banding). Surgical intervention may be required for third and fourth degree cases.

In the past, a wide variety of surgical methods have been suggested for the treatment of severe internal hemorrhoids. One method used in the United States is the Ferguson, or closed, hemorrhoidectomy. In the Ferguson procedure, a Ferguson-Hill retractor is inserted into the anus to obtain access to a hemorrhoidal site. The surgeon then clamps the hemorrhoid with alligator clamps, ligates the vessels, and dissects the hemorrhoid from the rectal wall with a scalpel or scissors. Once the hemorrhoid is removed, the surgical site is sutured closed. The retractor is rotated to another position and the remaining hemorrhoids are dealt with in a similar manner.

In general, European surgeons prefer the Milligan-Morgan, or open hemorrhoidectomy for the removal of internal hemorrhoids. In the Milligan-Morgan procedure, rather than using a retractor, the anus is gently dilated with two fingers and forceps are placed at the mucocutaneous junction of each primary hemorrhoid. The hemorrhoids are pulled down and a second forceps is applied to the main bulk of each hemorrhoid to produce "a triangle of exposure". Next, the clamped hemorrhoid is dissected from the sphincter muscle and is dissected proximally as far as the pedicles and then ligated or tied. Unlike the Ferguson procedure, the wound is not sutured closed, but is left open with a light dressing applied to the wound.

Another hemorrhoidectomy procedure is the Whitehead procedure. In this procedure, the hemorrhoidal tissue is excised above the dentate line and the redundant rectal mucosa is excised and sutured to the anoderm (the epithelial lining of the anal canal). This surgery is indicated for circumferential hemorrhoids. Several modifications of Whitehead exist, including raising the anoderm and suturing it to the rectal mucosa. This method is commonly avoided, since the procedure is thought to be difficult to perform, bloody, and susceptible to complications.

There was still a need for a simple, safe and fast method of performing a hemorrhoidectomy. The use of a conventional circular stapler to perform a hemorrhoidectomy on second and third degree hemorrhoids soon emerged. Typically, three fingers are used to dilate the anus and a continuous submucosal circle of suture are placed at the base of the dentate line. A curved needle is used to place the suture ring submucosally and the entry and exit point of the suture should be the same or nearly the same. Next, a conventional circular stapling instrument, having a stapling end effector, is opened by amply extending an anvil assembly away from a stapling head assembly. The opened stapling end effector is placed into the anus of a patient and positioned to place the anvil assembly of the stapling end effector distal to the suture ring and the stapling head assembly (of the stapling end effector) proximally outside the patient. This placement enables the surgeon to reach within the anus and to grasp the loose ends of the suture. The loose ends of the suture are drawn out of the anus and out of the stapling end effector between the open anvil and the stapling head assembly. The loose ends of the suture are then pulled upon to draw the circle of suture closed and to draw the anal tissue in around the anvil shaft connecting the open anvil to the stapling head assembly of the circular stapling instrument. Next, the surgeon tightly knots the suture about the anvil shaft and closes the anvil upon the hemorrhoidal mass. The loose ends of the suture protrude from the stapling end effector between the closed anvil and the stapling head assembly. The stapler is fired to perform a hemorrhoidal transection. Once fired, the circular stapling instrument is removed from the anus with the transected hemorrhoids captured within.

The firing of the circular stapler effectively transects the hemorrhoids and applies staples to the transection site. The use of staples as an effective fastening means is known in hemorrhoidal surgery. The hemorrhoidal transection typically occurs at the submucosal level and does not involve the muscular striae. Thus, this procedure offers surgeons an alternative to other conventional hemorrhoidal procedures such as those developed by Ferguson, Milligan-Morgan, and Whitehead.

One limitation of the procedure is the depth that the circular stapler can be placed into the anus. As described above, the open anvil assembly of the stapling end effector is placed distal to the suture ring and the stapling head assembly is placed proximally outside the patient. This enables the surgeon to grasp the loose ends of the suture and to draw the suture out of the anus through the gap between the anus and the stapling head assembly. The need for the gap to withdraw the suture from the anus limits the depth that the stapling end effector can be placed into the anus. If the hemorrhoids are located deeper into the anal canal, such as internal hemorrhoids, the stapling head assembly enters the anus and effectively blocks the surgeon from accessing the loose ends of the suture.

What is needed is a repair device or instrument that is not limited to external hemorrhoids but can access hemorrhoids wherever they exist. Such an instrument could effectively be used for the removal of internal hemorrhoids above the dentate line.

An additional limitation of the procedure is the amount of hemorrhoidal tissue that can be drawn into the stapling end effector of a conventional circular stapling instrument. Hemorrhoids are drawn into and around an anvil shaft (connecting the open anvil assembly to the stapling head assembly) by tightening a continuous loop of suture placed below the dentate line. This action draws the hemorrhoids around the anvil shaft but does not draw the hemorrhoids into the inner chamber of the stapling head assembly. This limits the amount of hemorrhoidal tissue that can be brought into the stapling end effector and the surgeon may remove part of a hemorrhoid. What is needed is a method of drawing the hemorrhoids around the anvil shaft and into the inner chamber of the stapling head assembly to ensure that more of the hemorrhoidal tissue is removed in a single firing of the circular stapling instrument.

At present, there are no known surgical instruments that can meet all of the needs outlined above. These and other advantages of the present disclosure will become more apparent from the following detailed description and drawings.

SUMMARY

The present disclosure provides a novel energy based partial circumferential hemorrhoid repair device which allows improved visibility of hemorrhoid tissue entering and being sealed by the device. The device of the present disclosure obviates the need for purse string placement, since hemorrhoid tissue may be drawn into the device through standard graspers, or by surrounding the hemorrhoid tissue within the hemorrhoid repair device assembly. The configuration of the energy based partial circumferential hemorrhoid repair device permits removal of individual hemorrhoids or specific regions, instead of the entire circumference. It is, however, contemplated that the partial circumferential hemorrhoid repair device may also be rotated, while in place, to remove hemorrhoid tissue about a full circumference.

In accordance with an embodiment of the present disclosure, an energy based partial circumferential hemorrhoid repair device is provided which includes an actuator assembly operatively connected to an energy based partial circumferential hemorrhoid repair device head assembly. The energy based repair device also includes a cord extending from the actuator assembly. The cord is connected to a source of electrosurgical energy.

The actuator assembly is connected to the hemorrhoid repair device head assembly via a series of co-axial tubes. Each tube is uniquely configured to cooperate with the actuator assembly on a proximal end and the energy based repair device head assembly on a distal end to effect cauterizing and cutting of a hemorrhoid.

The energy based repair device head assembly includes two electrode assemblies, a proximal electrode assembly and a distal electrode assembly. The proximal electrode assembly is slidably mounted on rails to allow for distal and proximal motion as the electrode assemblies are approximated and spaced apart and the distal electrode assembly is fixedly mounted on a distal portion of the rails.

Each of the electrode assemblies includes an arcuate electrode mounted on each of the opposing surfaces to facilitate sealing of the hemorrhoid tissue as the two electrode assemblies are approximated. The proximal electrode assembly defines an arcuate slot. A knife member is housed within the slot in the electrode assembly and is configured to move distally to sever the hemorrhoid tissue after the tissue is sealed by the electrodes.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description of the embodiments given below, serve to explain the principles of the disclosure.

FIG. 6a is a side cross-sectional detail view of the energy based partial circumferential hemorrhoid repair device assembly of FIG. 6 surrounding a hemorrhoid in accordance with an embodiment of the present disclosure;

FIG. 6b is a perspective detail view of the energy based partial circumferential hemorrhoid repair device head assembly surrounding a hemorrhoid in accordance with an embodiment of the present disclosure;

FIG. 7a is a side cross-sectional detail view of the energy based partial circumferential hemorrhoid repair device assembly surrounding and cauterizing a hemorrhoid in accordance with an embodiment of the present disclosure;

FIG. 7b is a perspective detail view of the energy based partial circumferential hemorrhoid repair device head assembly surrounding and cauterizing a hemorrhoid in accordance with an embodiment of the present disclosure;

DETAILED DESCRIPTION OF EMBODIMENTS

Figure 1:
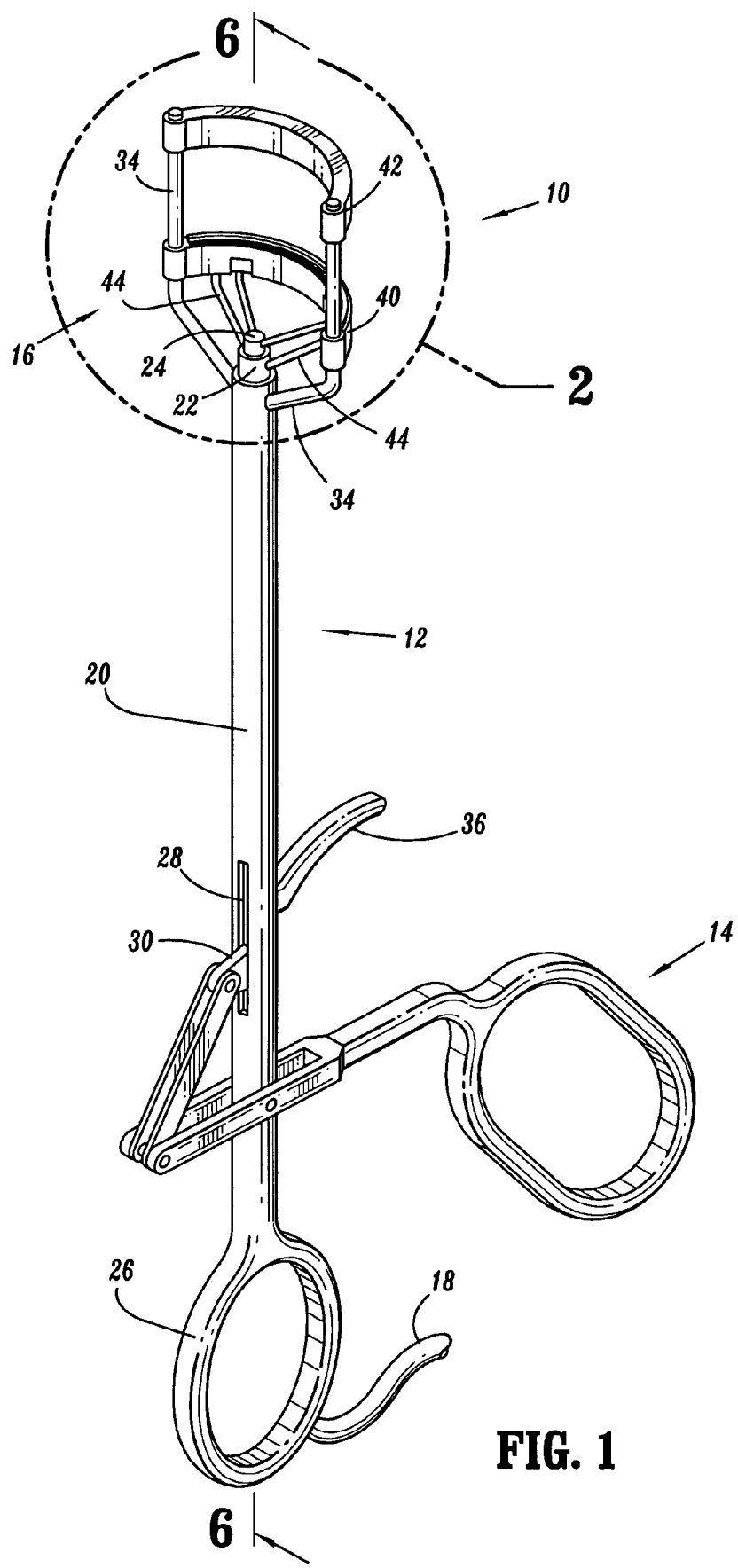
FIG. 1 is a perspective view of an energy based partial circumferential hemorrhoid repair device in accordance with an embodiment of the present disclosure.

Embodiments of the presently disclosed energy based partial circumferential hemorrhoid repair device will now be described in detail with reference to the figures, in which like reference numerals identify corresponding elements throughout the several views.

In the description that follows, as is traditional, the term "proximal" will refer to the end of the surgical instrument closest to the operator and the term "distal" will refer to the end of the surgical instrument furthest from the operator.

An energy based partial circumferential hemorrhoid repair device, shown generally as reference numeral 10 in FIG. 1, includes a generally tubular portion 12 having an actuator assembly 14 on a proximal end thereof and an energy based partial circumferential hemorrhoid repair device head assembly 16 on a distal end thereof. Energy based repair device 10 also includes an electrical cord 18 extending from a proximal end of actuator assembly 14 and is further connected to a source of electrosurgical energy (not shown), as is known to one having ordinary skill in the art. It is contemplated that tubular portion 12 may be configured in a plurality of shapes and sizes, each defining an internal bore.

Tubular portion 12 includes a plurality of co-axial tubes. Each tube is configured to cooperate with actuator assembly 14 on a proximal end and the energy based repair device head assembly 16 on a distal end, to effect cutting and cauterizing of a hemorrhoid, as will be described in further detail herein. In the embodiment illustrated, beginning in FIG. 1, tubular portion 12 includes outer tube 20, a middle tube 22 and an inner tube or rod 24.

The outer tube 20-defines a lumen which is configured and dimensioned to receive middle tube 22 and inner tube 24 therein. The outer tube 20 terminates on a proximal end with a ring shaped member 26 which forms a portion of the actuator assembly 14. The ring shaped member 26 is dimensioned to receive a finger from the surgeon to move the actuator assembly 14. The ring shaped member is illustrated monolithically formed with outer tube 20. However, it is contemplated that ring shaped member 26 and/or actuator assembly 14 may be formed independently and connected to outer tube 20.

Outer tube 20 defines a first longitudinal slot 28 to permit the actuator assembly 14 to access the middle tube 22 such that actuation of the actuator assembly causes movement of the middle tube 22 in the longitudinal direction. As will be described in further detail, a post member 30 is connected to middle tube 22 and extends through slot 28 where the post member 30 is pivotally connected to linkage associated with the actuator assembly 14. Outer tube 20 further defines a second longitudinal slot 32 (see FIG. 6) to permit longitudinal movement of a knife actuation lever assembly 36.

The distal portion of outer tube 20 terminates at the energy based repair device head assembly 16. Two substantially L-shaped rails 34 are connected to a distal end portion of outer tube 20. The L-shaped rails 34 extend substantially perpendicular to, and distally from, the distal end portion of outer tube 20.

Energy based repair device head assembly 16 includes two electrode assemblies, a proximal electrode assembly 40 and a distal electrode assembly 42. Each of the two electrode assemblies has an arcuate shape and does not form a complete circle. The proximal electrode assembly 40 is slidably mounted on rails 34 to allow for distal and proximal motion as the electrode assemblies 40 and 42 are approximated and spaced apart. To facilitate movement of the proximal electrode assembly 40, thereby approximating and separating the two electrode assemblies 40 and 42, proximal electrode assembly 40 is connected to middle tube 22 via a pair of electrode assembly support struts 44. Further details of the approximation of the electrode assemblies are described below. The distal electrode assembly 42 is fixedly mounted on a distal portion of rails 34.

Figure 2:
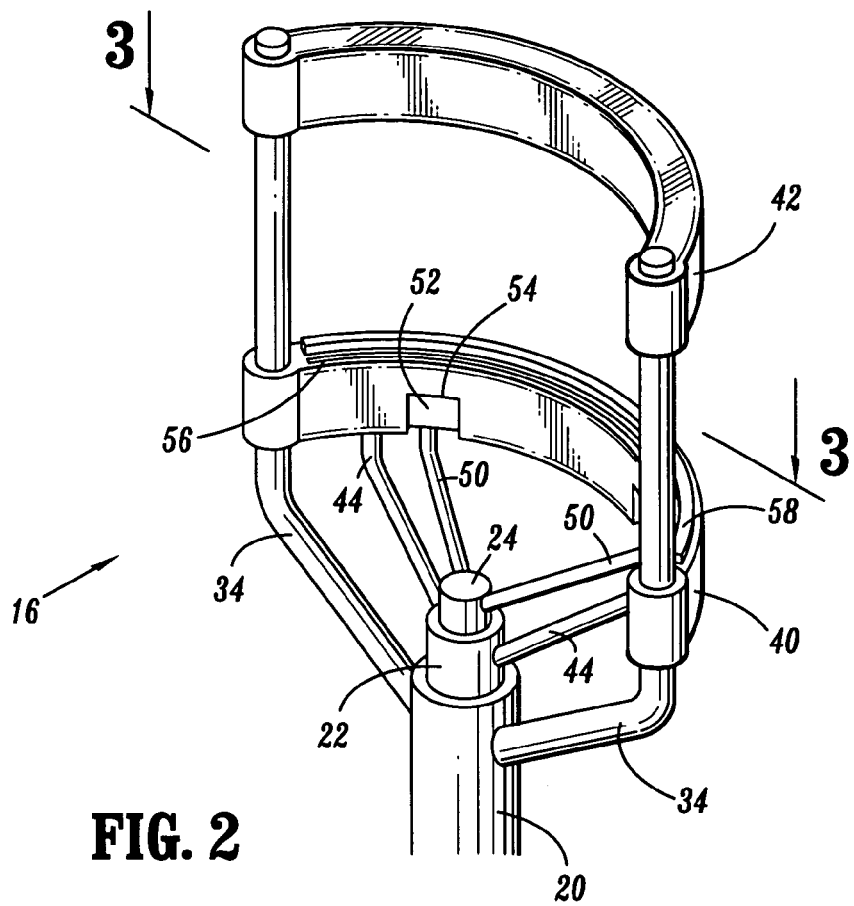
FIG. 2 is a detail view of the energy based partial circumferential hemorrhoid repair device head assembly of FIG. 1 in accordance with an embodiment of the present disclosure.

Referring now to FIG. 2, a detail view of an energy based partial circumferential hemorrhoid repair device head assembly in accordance with an embodiment of the present disclosure is illustrated. As described above, energy based repair device head assembly 16 includes two electrode assemblies, a proximal electrode assembly 40 and a distal electrode assembly 42. The proximal electrode assembly 40 is slidably mounted on rails 34 to allow for distal and proximal motion as the electrode assemblies 40 and 42 are approximated and spaced apart, and the distal electrode assembly 42 is fixedly mounted on a distal portion of rails 34. It is envisioned that assembly 42 may be movable along rails 34 and electrode assembly 40 may be fixedly mounted.

Each of the electrode assemblies 40 and 42 includes an arcuate electrode 58 mounted on opposing surfaces to facilitate sealing of the hemorrhoid tissue as the two electrode assemblies are approximated and energized. The proximal electrode assembly 40 defines an arcuate slot 56 (best seen in FIG. 3 which is a top view along line 3-3 of energy based partial circumferential hemorrhoid repair device head assembly illustrated in FIG. 2). A knife member 52 is housed within slot 56 and is configured to move distally to cut the hemorrhoid tissue after the tissue is sealed by the electrodes 58. The proximal edge of knife member 52 is connected to a first end of two knife support struts 50. Second ends of the two knife support struts 50 are connected to inner tube 24. Therefore, distal movement of inner tube 24 will cause distal movement of knife member 52. A cutout is provided in an inner wall of electrode assembly 40 to provide clearance for struts 50 to move distally. Alternatively, struts 50 could be reconfigured such that the portion of the strut that is in the same plane as knife member 52 is dimensioned in both length and width to be capable of entering the slot 56 and moving knife member 52 a predetermined distance.

Figure 3:
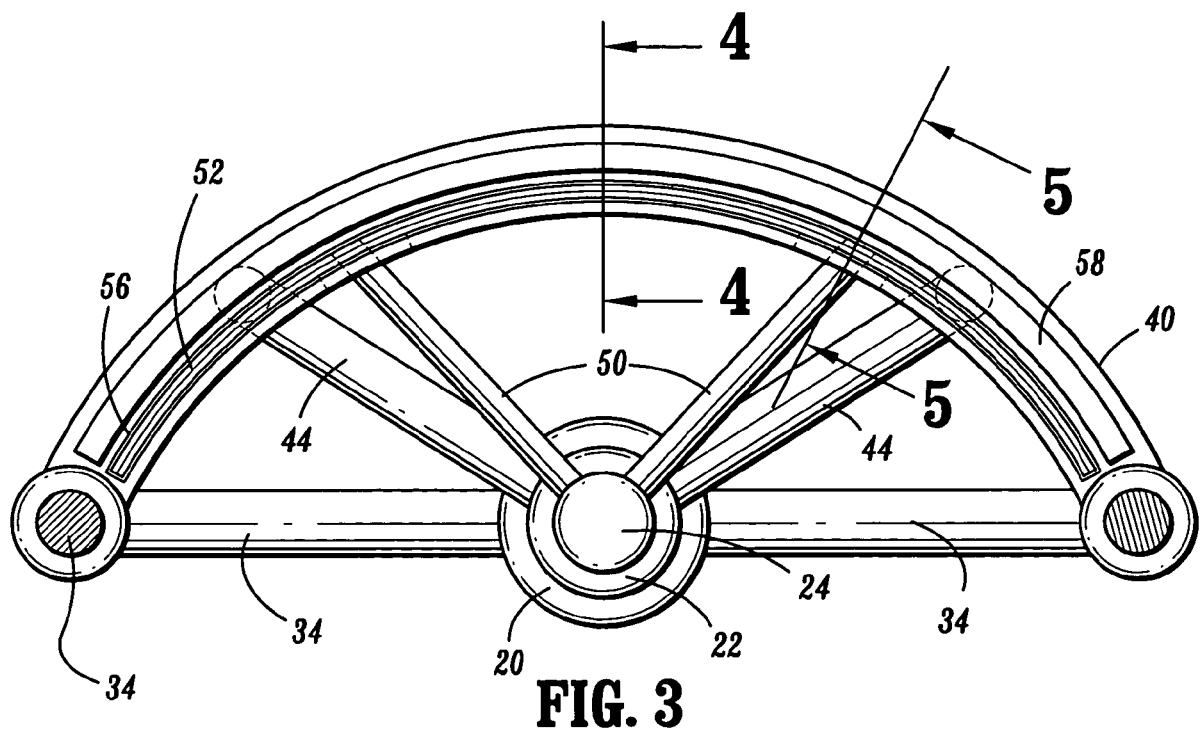
FIG. 3 is a top view of the energy based partial circumferential hemorrhoid repair device head assembly illustrated in FIG. 2.
Figure 4:
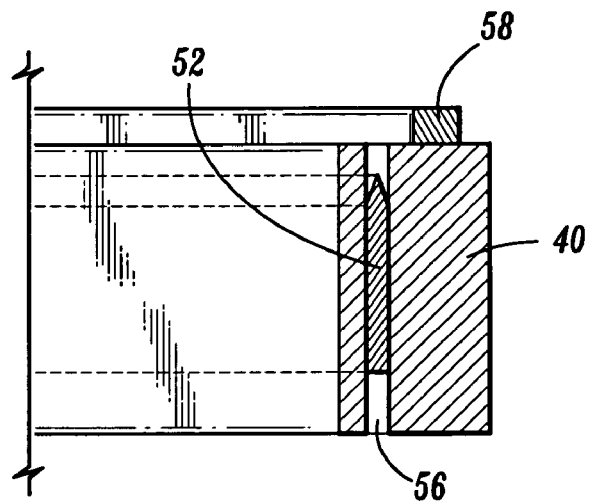
FIG. 4 is a side cross-sectional view of the proximal electrode assembly illustrated in FIG. 3.
Figure 5:
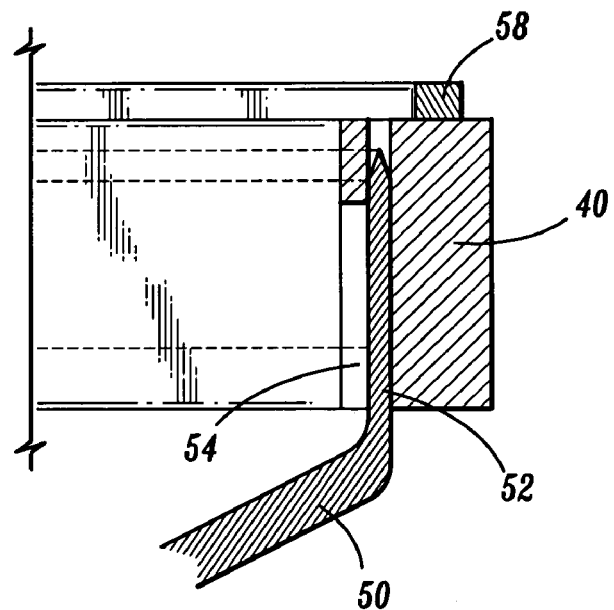
FIG. 5 is a side cross-sectional view of the proximal electrode assembly illustrated in FIG. 3.

FIGS. 4 and 5 are side cross-sectional views along lines 4-4 and 5-5, respectively, of the proximal electrode assembly 40, having an electrode 58 mounted on a surface thereof, illustrated in FIG. 3. FIGS. 4 and 5 illustrate the position of the knife member 52 within slot 56. In each of the figures, knife member 52 is illustrated in the proximal, non-deployed, position. FIGS. 4 and 5 differ due to the location of the cut line in FIG. 3. That is, the cut line for FIG. 5 is positioned such that at least a portion of support strut 50 is illustrated while FIG. 4 does not include the strut.

Figure 6:
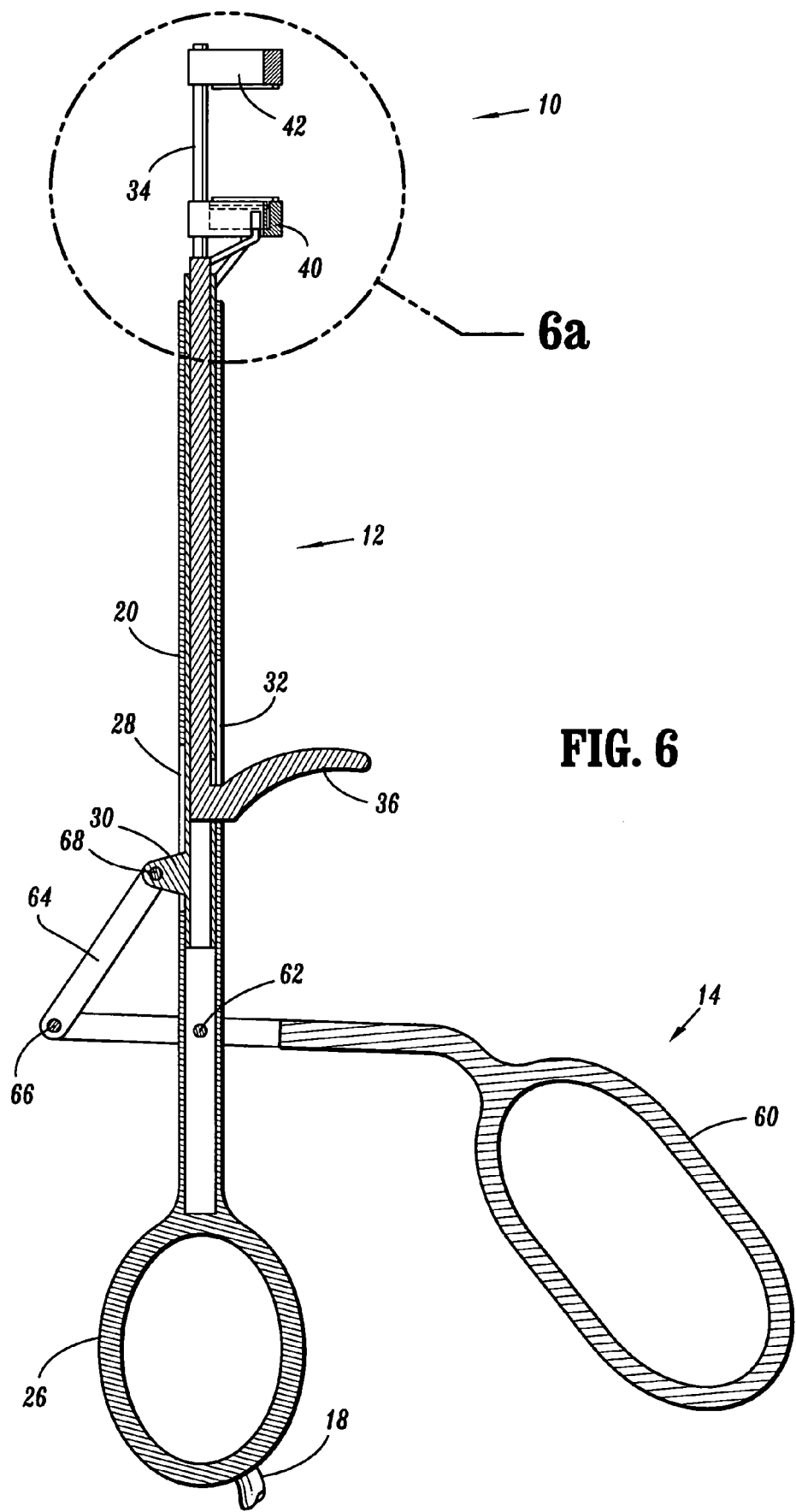
FIG. 6 is a side cross-sectional view of the energy based partial circumferential hemorrhoid repair device assembly in accordance with an embodiment of the present disclosure.

FIG. 6 is a side cross-sectional view of the energy based partial circumferential hemorrhoid repair device assembly in an undeployed position, prior to being positioned around hemorrhoid tissue. Actuator assembly 14 includes two substantially ring shaped members 26 and 60. Ring shaped member 26 forms the proximal end of tube 20. Ring shaped member 60 is pivotally connected to tubular portion 12 by pin 62. Pins 66 and 68 pivotally connect ring-shaped member 60 to linkage 64, and linkage 64 to post member 30, respectively. Post member 30 is connected to middle tube 22 to transfer the forces from the actuator assembly, through linkage 64, to middle tube 22. The forces that are translated to middle tube 22 cause the proximal electrode assembly 40 to slide on rail 34 toward electrode assembly 42.

FIGS. 6a and 6b are detail views of the energy based partial circumferential hemorrhoid repair device head assembly 16 surrounding a hemorrhoid 72 (shown in phantom), prior to the electrode assemblies 40 and 42 being approximated. Hemorrhoid tissue 72 is pulled into the energy based repair device using standard graspers (not shown) or by other means known to one having ordinary skill in the art. It is also contemplated that the hemorrhoid repair device may be used to repair the hemorrhoid by tightening the mucosa tissue adjacent to the hemorrhoid.

Figure 7:
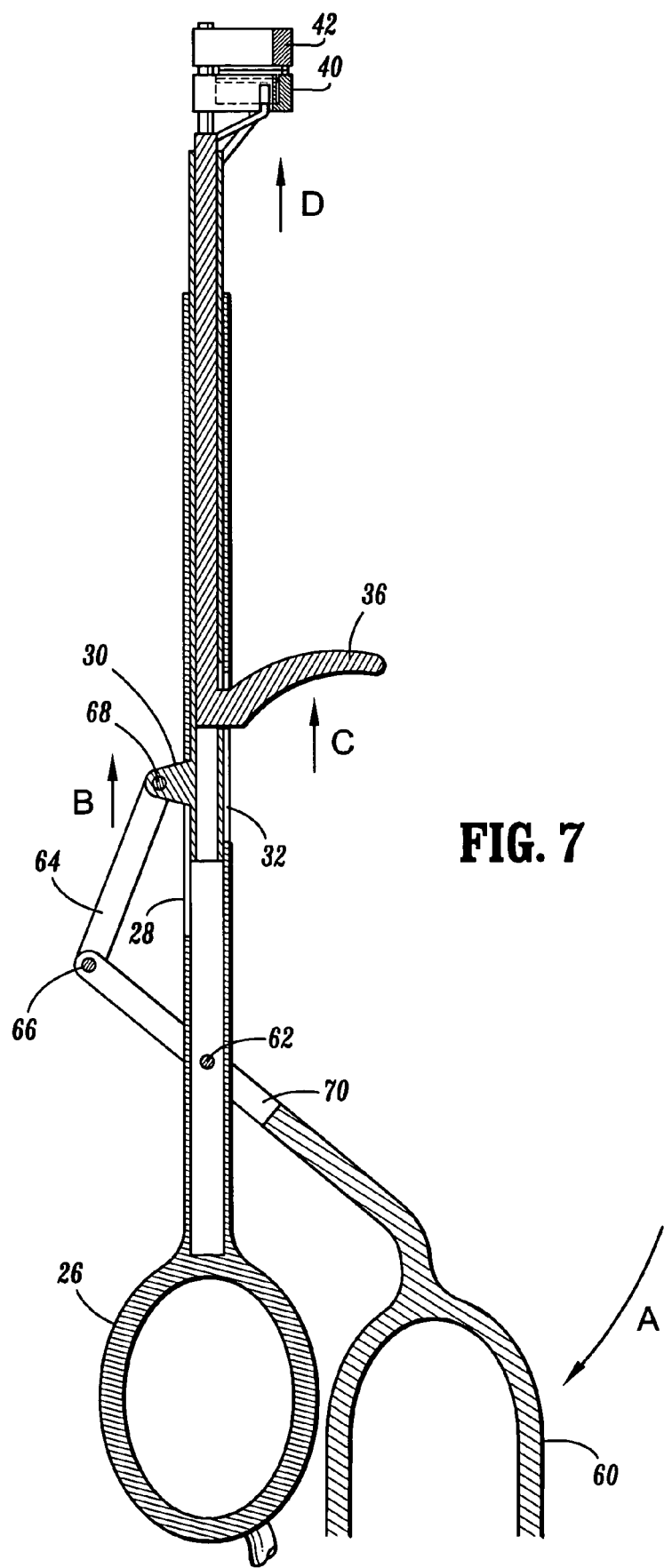
FIG. 7 is a side cross-sectional view of the energy based partial circumferential hemorrhoid repair device assembly illustrating the direction of movement of the several components in accordance with an embodiment of the present disclosure.

FIG. 7 is a side cross-sectional view of the energy based partial circumferential hemorrhoid repair device assembly illustrating the direction of movement of the several components during use of the instrument. Once the surgeon has the instrument in position with hemorrhoidal tissue between the electrode assemblies (as illustrated in FIGS. 6a and 6b), the two ring shaped members 26 and 60 of the actuator assembly 14 are approximated in the direction indicated by arrow A. More specifically, as ring shaped member 60 is moved in the direction of arrow A, and ring member 26 is held stationary, arm 70 pivots about pin 62 such that the distal end of arm 70 forces linkage 64 to move distally through the pivotal connection at pin 66. Linkage 64 is pivotally connected to post member 30 via pin 68. The force applied through pin 68 via linkage 64 causes post member 30 to move distally within slot 28, in the direction indicated by arrow B. Post member 30 continues to move in the distal direction until it reaches the end of slot 28. When post member 30 hits the end of slot 28, electrode assemblies 40 and 42 are in the approximated position.

However, as illustrated in FIG. 7, at this point, knife actuation lever assembly 36 has not reached the end of slot 32. The knife is actuated separately in the direction of arrows C and D, after the hemorrhoid tissue is cauterized and sealed by the electrodes 58 on electrode assemblies 40 and 42. The knife is actuated by driving the knife actuation lever assembly 36 in the distal direction. The difference between the length of slot 32 and the length of slot 28 permits the knife actuation lever assembly 36 to be driven distally a distance required for the knife to sever the hemorrhoid tissue 72 adjacent to the line of cauterization.

It is also contemplated that the knife is biased for distal movement (for example, spring loaded) in response to movement of a trigger assembly. In such an embodiment, knife actuation lever assembly 36 is replaced by a trigger assembly which, when activated, releases the knife and permits it to move distally to sever the unwanted hemorrhoid tissue.

FIGS. 7a and 7b are views of the energy based partial circumferential hemorrhoid repair device assembly surrounding and sealing a hemorrhoid in accordance with an embodiment of the present disclosure. As illustrated in FIGS. 7a and 7b, as middle tube 22 moves distally in the direction of arrows E, proximal electrode assembly 40 is moved distally along rails 34 due to the connection between middle tube 22 and electrode assembly 40 via support struts 44. As electrode assemblies 40 and 42 are approximated, hemorrhoid tissue 72 is captured between electrodes 58. To seal the hemorrhoid tissue, the electrodes 58 are energized with, for example, radio frequency (RF) energy, or another electrical energy source as is known to one having ordinary skill in the art. A generator (not shown) supplies the electrosurgical energy to electrodes 58. Virtually any generator which provides electrosurgical energy for medical applications may be used with the present invention. Preferably, the generator is a voltage determinative, low source impedance generator which provides RF energy. The preferred RF range is about 100 to 1,000 kHz.

Figures 8, 8A:
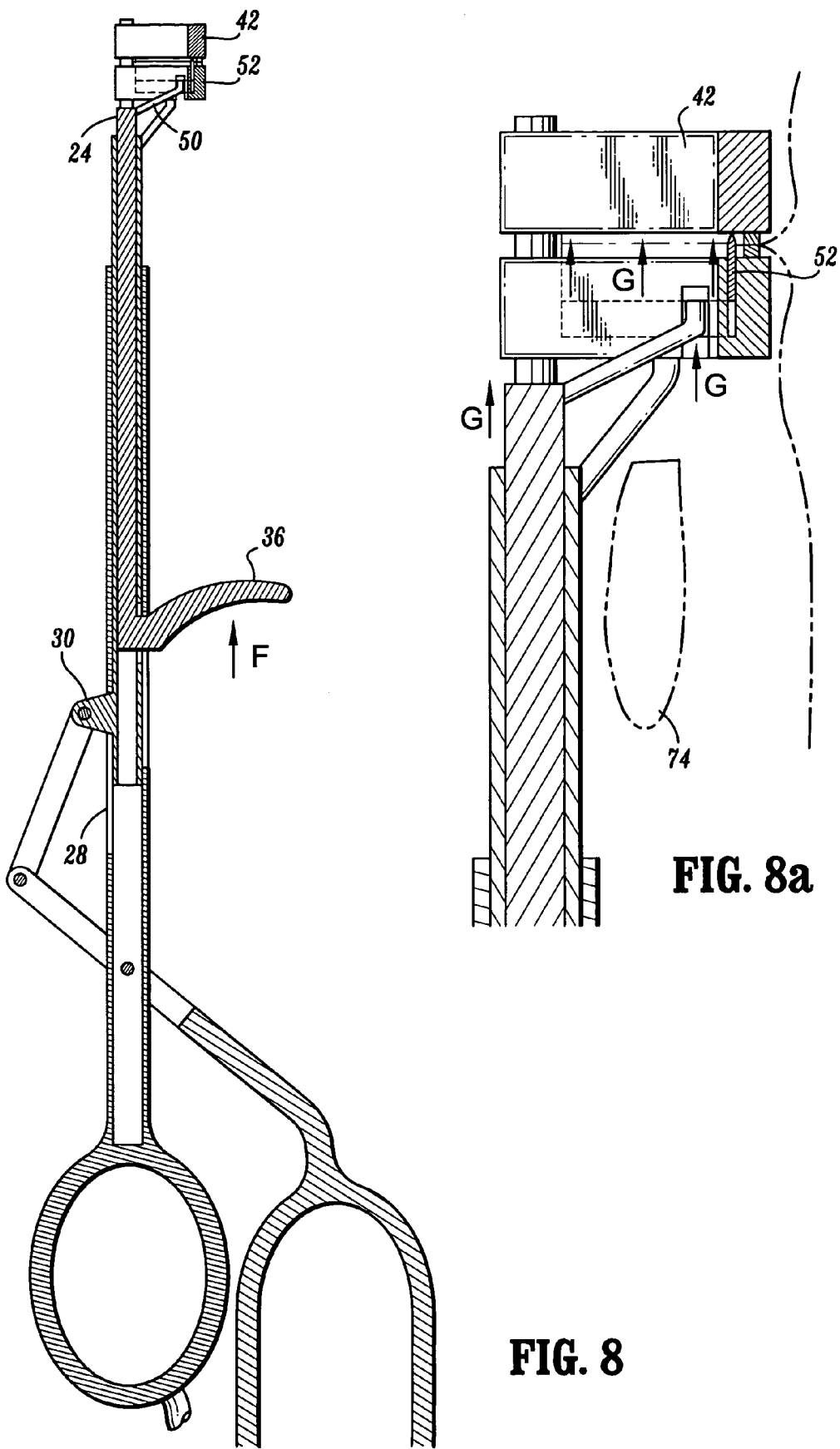
FIG. 8 is a side cross-sectional view of the energy based partial circumferential hemorrhoid repair device assembly illustrating the direction of movement of the knife assembly in accordance with an embodiment of the present disclosure.
FIG. 8a is a side cross-sectional detail view of the energy based partial circumferential hemorrhoid repair device assembly illustrating the direction of movement of the knife in accordance with an embodiment of the present disclosure.

FIG. 8 is a side cross-sectional view of the energy based partial circumferential hemorrhoid repair device assembly illustrating the movement of the knife assembly in accordance with an embodiment of the present disclosure. As described above, once anchor 30 reaches the distal-most end of slot 28, knife actuation lever assembly 36 may be driven distally in the direction of arrow F to drive knife 52 distally via inner tube 24 and support struts 50.

FIG. 8a is a side cross-sectional detail view of the energy based partial circumferential hemorrhoid repair device assembly illustrating the direction of movement of the knife 52 in accordance with an embodiment of the present disclosure. The knife 52 is moved distally, as described above, in the direction of arrow G. When knife 52 is at its distal-most position, the hemorrhoid tissue is caught in a space defined by the sharpened distal edge of knife 52 and the lower surface of electrode assembly 42. The hemorrhoid tissue is severed by knife 52. The severed portion 74 of hemorrhoid tissue is then removed.

Advantages of the present disclosure include improved visibility of hemorrhoid tissue entering and being sealed by the device. The device of the present disclosure obviates the need for purse string placement, since hemorrhoid tissue may be drawn into the device through standard graspers, or by surrounding the hemorrhoid tissue within the hemorrhoid repair device assembly. The configuration of the energy based partial circumferential hemorrhoid repair device permits removal of individual hemorrhoids or specific regions instead of the entire circumference. The partial circumferential hemorrhoid repair device may also be rotated, while in place, to remove hemorrhoid tissue about a full circumference.

It will be understood that various modifications may be made to the embodiments disclosed herein. Therefore, the above description should not be construed as limiting, but merely as exemplifications of various embodiments. Those skilled in the art will envision other modifications within the scope and spirit of the following claims.

What is claimed is:

1. An energy based partial circumferential hemorrhoid repair device comprising:
a tubular portion including a first longitudinal slot defining a first length and a second longitudinal slot defining a second length, the first length being different from the second length;
an actuator assembly positioned at a proximal end of the tubular portion;
an energy based partial circumferential hemorrhoid repair device head assembly operatively connected to the actuator assembly, wherein the head assembly includes a proximal electrode assembly having an arcuate slot and a distal electrode assembly, and further wherein at least one of the electrode assemblies includes an electrode mounted thereon to facilitate sealing of hemorrhoid tissue as the two electrode assemblies are approximated;
a knife member housed within the arcuate slot and configured for longitudinal movement to sever the hemorrhoid tissue; and
a plurality of struts interposed between and connecting the tubular portion and the head assembly.

2. The energy based partial circumferential hemorrhoid repair device as recited in claim 1, wherein each of the electrode assemblies includes an arcuate electrode mounted on opposing surfaces to facilitate sealing of the hemorrhoid tissue as the two electrode assemblies are approximated.

3. The energy based partial circumferential hemorrhoid repair device as recited in claim 1, wherein the knife member is configured to move distally to sever the hemorrhoid tissue after the tissue is sealed by the electrode assemblies.

4. The energy based partial circumferential hemorrhoid repair device as recited in claim 1, wherein the proximal electrode assembly is slidably mounted on rails to allow for distal and proximal motion as the electrode assemblies are approximated and spaced apart.

5. The energy based partial circumferential hemorrhoid repair device as recited in claim 4, wherein the distal electrode assembly is fixedly mounted on a distal portion of the rails.

6. The energy based partial circumferential hemorrhoid repair device as recited in claim 1, further comprising means for connecting the repair device to a source of electrosurgical energy.

7. The energy based partial circumferential hemorrhoid repair device as recited in claim 1, wherein the tubular portion includes a plurality of co-axial tubes.

8. The energy based partial circumferential hemorrhoid repair device as recited in claim 7, further including a knife actuation assembly associated with the knife member, the knife actuation assembly being configured to facilitate movement of the knife member.

9. The energy based partial circumferential hemorrhoid repair device as recited in claim 8, wherein the plurality of co-axial tubes includes an inner tube, a middle tube, and an outer tube, the inner tube being disposed within the middle tube, the middle tube being disposed within the outer tube.

10. The energy based partial circumferential hemorrhoid repair device as recited in claim 9, wherein the first longitudinal slot and the second longitudinal slot are formed in the outer tube, the second longitudinal slot being configured to receive a portion of the knife actuation assembly.

11. The energy based partial circumferential hemorrhoid repair device as recited in claim 10, wherein a difference between the first length and the second length permits movement of the knife member to sever the hemorrhoid tissue adjacent a line of cauterization defined by the electrode.

12. The energy based partial circumferential hemorrhoid repair device as recited in claim 9, wherein the middle tube is configured for longitudinal movement through the outer tube, and the inner tube is configured for longitudinal movement through the middle tube.

13. The energy based partial circumferential hemorrhoid repair device as recited in claim 12, wherein the middle tube is operably connected to the actuator assembly such that movement of the actuator assembly causes longitudinal movement of the middle tube.

14. The energy based partial circumferential hemorrhoid repair device as recited in claim 13, wherein the proximal electrode assembly is operably connected to the middle tube such that longitudinal movement of the middle tube causes corresponding movement of the proximal electrode assembly.

15. The energy based partial circumferential hemorrhoid repair device as recited in claim 12, wherein the knife member is operably connected to the inner tube such that distal movement of inner tube causes corresponding movement of the knife member.

16. The energy based partial circumferential hemorrhoid repair device as recited in claim 1, wherein the plurality of struts includes at least one strut interposed between and connecting the tubular portion and the knife member to facilitate movement of the knife member.

17. The energy based partial circumferential hemorrhoid repair device as recited in claim 1, wherein the plurality of struts includes at least one strut interposed between and connecting the tubular portion and the proximal electrode assembly to facilitate movement of the proximal electrode assembly.

18. The energy based partial circumferential hemorrhoid repair device as recited in claim 1, wherein the arcuate slot housing the knife member defines an arc less than 180°.

19. The energy based partial circumferential hemorrhoid repair device as recited in claim 1, wherein the head assembly is configured and dimensioned to define an axis of symmetry extending collinearly with a longitudinal axis of the tubular portion.

20. The energy based partial circumferential hemorrhoid repair device as recited in claim 1, wherein the plurality of struts are tubular in configuration.

21. The energy based partial circumferential hemorrhoid repair device as recited in claim 1, wherein the plurality of struts are spaced circumferentially.

22. A method of repairing a hemorrhoid, comprising the steps of:
  providing an energy based repair device including:
    a tubular portion including a first longitudinal slot defining a first length and a second longitudinal slot defining a second length, the first length being different from the second length;
    an actuator assembly positioned at a proximal end of the tubular portion;
    a head assembly operatively connected to the actuator assembly and having at least one electrode to facilitate cauterization of hemorrhoid tissue; and
    a knife member housed within the head assembly and being configured for longitudinal movement to sever the hemorrhoid tissue; and
    a plurality of struts interposed between and connecting the tubular portion and the head assembly;
  connecting the energy based repair device to an energy source to selectively energize the head assembly;
  cauterizing the hemorrhoid tissue with the head assembly; and
  severing the hemorrhoid tissue with the knife member.

23. The method of claim 22, wherein the step of providing an energy based repair device includes providing an energy based repair device having a head assembly that is repositionable between a first position, in which the head assembly is configured to receive the hemorrhoid tissue, and a second position, in which the head assembly is configured to cauterize the hemorrhoid tissue.

24. The method of claim 23, wherein the step of providing an energy based repair device includes providing an energy based repair device having a head assembly with proximal and distal electrode assemblies, the proximal and distal electrode assemblies being spaced apart when the head assembly is in the first position and substantially approximated when the head assembly is in the second position.

25. The method of claim 24, wherein the step of cauterizing the hemorrhoid tissue includes approximating the proximal and distal electrode assemblies.

26. The method of claim 22, wherein the step of severing the hemorrhoid tissue includes moving the knife member longitudinally subsequent to cauterization of the hemorrhoid tissue to sever the hemorrhoid tissue adjacent a line of cauterization defined by the electrode.

* * * * *

UNITED STATES PATENT AND TRADEMARK OFFICE
CERTIFICATE OF CORRECTION

PATENT NO.       : 7,608,073 B2                                                Page 1 of 1
APPLICATION NO.  : 11/170812
DATED            : October 27, 2009
INVENTOR(S)      : Heinrich et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 980 days.

Signed and Sealed this

Twelfth Day of October, 2010

David J. Kappos
*Director of the United States Patent and Trademark Office*